(12) United States Patent
Ackermann et al.

(10) Patent No.: US 8,552,719 B2
(45) Date of Patent: Oct. 8, 2013

(54) METHOD AND APPARATUS FOR THE PURIFICATION AND ANALYTICAL EVALUATION OF HIGHLY PURIFIED LIQUIDS

(75) Inventors: Arthur John Ackermann, St. Louis, MO (US); Glen Walter Wildermuth, St. Louis, MO (US); David Brian Blackford, North Oaks, MN (US)

(73) Assignee: Microfier, Inc., St. Louis, MO (US)

( * ) Notice: Subject to any disclaimer, the term of this patent is extended or adjusted under 35 U.S.C. 154(b) by 315 days.

(21) Appl. No.: 12/849,165

(22) Filed: Aug. 3, 2010

(65) Prior Publication Data
US 2011/0025306 A1 Feb. 3, 2011

Related U.S. Application Data

(60) Provisional application No. 61/230,971, filed on Aug. 3, 2009, provisional application No. 61/257,700, filed on Nov. 3, 2009, provisional application No. 61/306,208, filed on Feb. 19, 2010, provisional application No. 61/366,473, filed on Jul. 21, 2010.

(51) Int. Cl.
*G01N 27/82* (2006.01)
(52) U.S. Cl.
USPC .......................................................... 324/240
(58) Field of Classification Search
USPC .............. 324/204; 210/695–770, 222, 223; 204/671
See application file for complete search history.

(56) References Cited

U.S. PATENT DOCUMENTS

| | | | |
|---|---|---|---|
| 4,024,047 A | 5/1977 | Clark et al. | |
| 5,128,043 A * | 7/1992 | Wildermuth | 210/695 |
| 5,328,572 A | 7/1994 | Ibbott | |
| 5,614,088 A | 3/1997 | Nagai et al. | |
| 5,807,473 A | 9/1998 | Sadler et al. | |
| 6,274,040 B1 | 8/2001 | Mitsumori et al. | |
| 6,312,597 B1 | 11/2001 | Mohindra et al. | |
| 7,572,359 B2 | 8/2009 | Liang et al. | |
| 7,578,919 B2 | 8/2009 | Pitts, Jr. et al. | |
| 7,582,198 B2 | 9/2009 | Wilkins et al. | |
| 7,604,725 B2 | 10/2009 | Ganzi et al. | |
| 7,658,828 B2 | 2/2010 | Freydina | |

FOREIGN PATENT DOCUMENTS

| | | |
|---|---|---|
| JP | 10-47036 A | 2/1998 |
| JP | 2006-88144 A | 4/2006 |
| KR | 10-0463726 B1 | 12/2004 |

OTHER PUBLICATIONS

International Search Report and Written Opinion from corresponding International Appln. No. PCT/US2010/044214 mailed Mar. 23, 2011.

* cited by examiner

*Primary Examiner* — Arleen M Vazquez
*Assistant Examiner* — Alesa Allgood
(74) *Attorney, Agent, or Firm* — Polster, Lieder, Woodruff & Lucchesi, L.C.

(57) ABSTRACT

A method and apparatus for removing soluble and insoluble contaminants from highly purified and ultra-pure liquids having a bulk resistivity in excess of one megohm-centimeter by establishing laminar flow of the liquid in a cylindrical chamber through an electromagnetic field transverse to the direction of flow, to induce mobility of the constituents. The wall of the chamber forms a cathode and a central rod forms an anode in the chamber. The mobilized constituents are transported either to the anode or the cathode, where the material will adhere and agglomerate with other constituents. Systems are provided utilizing the method and apparatus for purifying and analytically evaluating highly purified and ultra-pure water.

39 Claims, 9 Drawing Sheets

METHOD AND APPARATUS FOR THE PURIFICATION AND ANALYTICAL EVALUATION OF HIGHLY PURIFIED LIQUIDS

CROSS-REFERENCE TO RELATED APPLICATIONS

Priority is claimed to U.S. Provisional Applications 61/230,971, filed Aug. 3, 2009, 61/257,700, filed Nov. 3, 2009, 61/306,208, filed Feb. 19, 2010, and 61/366,473, filed Jul. 21, 2010, the disclosures of which are hereby incorporated by reference.

STATEMENT REGARDING FEDERALLY SPONSORED RESEARCH

Not applicable.

BACKGROUND OF THE INVENTION

1. Technical Field

The invention relates to the removal of constituents from highly purified liquids, such as ultra-pure water, with a bulk resistivity in excess of one megohm-centimeter.

2. Background Art

Highly purified and ultra-pure water is produced by a series of unit processes that progressively remove suspended and dissolved constituents. These processes, when operated properly, produce water that contains only trace amounts of contamination and that can be utilized in various industrial applications where highly purified water is critical to operation of systems and manufacturing of various products. This type of water quality is particularly important to, but not limited to, industries and research activities related to semiconductors, pharmaceuticals, photovoltaics, metal plating, power generation and nanotechnology.

As industries have increased operational efficiency and product quality, there has been an increase in requirements for higher quality liquids and analytical capabilities to measure the quality of high purity liquids.

Currently, the best available technologies for the removal of trace amounts of insoluble and soluble contamination in highly purified water is sub-micron membrane filtration or ultrafiltration. Membrane filtration and ultrafiltration have demonstrated the ability to remove particles as small as 10 nm and reject soluble material with a molecular weight cutoff of 13,000. However, membrane technology is reaching the limit of its capability, because smaller pores or membrane selectivity will make it difficult to pass water molecules with a diameter of 0.3 nm. Furthermore, the filter membrane material may deteriorate and shed particles from the physical impact of abrasive particles and the chemical attack by purified water. It may be noted that highly purified and ultra-pure liquids can be highly reactive and aggressive solvents.

It is particularly difficult for filters to control organic or biological particles because with large surface areas and extended service, bacteria may form significant colonies on the surface of the membranes, in voids ("dead legs"), low flow areas, and on the downstream side of the membranes ("grow through"). Once established on the product side of the membrane, the bacteria colonies will multiply and slough off randomly into the product stream, contaminating the highly purified liquids. Moreover, even biological particles that remain on the upstream side of the membrane eventually dissociate or disintegrate, contributing smaller particles that pass through the membranes, releasing organic contamination into the product stream. Finally, membrane filters can be cleaned only with cleaning solutions which are themselves likely to be contaminated, or with disassembly and back flushing or replacement which can introduce new contaminates. Thus, it can be appreciated that membrane filtration and ultrafiltration may actually exacerbate the problem of removing trace contamination from highly purified and ultra-pure liquids.

Currently, the best available technologies for the measurement of particles within high purity and ultrapure liquids are the optical particle counter (OPC) and slipstream collection of particles on sub-micron filter, in combination with scanning electron microscopy/energy dispersive X-ray spectroscopy (SEM/EDS).

The smallest particle size detected by the OPC is 40 nm and the detection limit is not likely to improve because of the fundamental limits of laser light wavelength and light scattering. Importantly, this size limitation is larger than the capability of membrane filtration or ultrafiltration, and therefore is only used to detect significant system upsets and not as a process control instrument.

As an alternative to OPC, a small (approximately 50 to 100 ml/min) stream of liquid can be filtered through a 25 mm membrane with 50, 100, or 200 nm pores to collect particles. This process will require significant time to collect an adequate amount of particles. For example, it takes approximately three weeks of slipstream filtration in an ultra-pure water system to collect an adequate number of particles. Once particles have been collected, the sample filter can be removed and evaluated by SEM/EDS to determine particle concentration, particle size distribution, and elemental composition of the particles. This analytical procedure can only effectively examine particles larger than 50 nm and is ineffective as a process control instrument because of the three-week lag time associated with the collection period. Further, due to the limitation of SEM/EDS, this analytical technique will not reliably evaluate the elemental composition of particles that are less than 100 nm.

The limitations of the current best practices for the purification and analytical evaluation of highly purified and ultra-pure liquids described above are problems for all industries utilizing these liquids for utility operations and manufacturing. This situation is particularly relevant in the semiconductor industry where critical particle size in advanced manufacture facilities is now 16 nm (half the 32 nm line width used to conduct electricity within semiconductor devices).

SUMMARY OF THE INVENTION

The present invention effectively captures and agglomerates soluble and insoluble constituents of all sizes from highly purified and ultra-pure liquids. As a result, this invention provides a new method and apparatus for purifying and analytically evaluating liquids that exceeds current practices.

This invention provides a new method and apparatus for purifying and analytically evaluating liquids with a bulk resistivity of greater than one megohm-centimeter. It has particular applicability to the further purification of ultra-pure water, having a resistivity of from about one to about eighteen megohm-centimeters. The method and apparatus of the instant invention operate pursuant to the discovery that particles, nano-particles, colloids, molecules, and ions in highly purified liquids typically exhibit a natural charge or charge polarity. This discovery has led to the novel method and apparatus of the present invention wherein both soluble and insoluble constituents can be removed from highly purified liquids.

The invention relates to the removal of constituents from highly purified liquids having a bulk resistivity in excess of one megohm-centimeter and more particularly, a method, apparatus, and embodiments for the removal of soluble and insoluble (dissolved and suspended) constituents from water such as particles, nano-particles, colloids, molecules, and ions. Additional embodiments for other high resistivity liquids can easily be extrapolated from this disclosure.

Since the electronics and semiconductor industry has the most stringent water quality requirements, this invention will find immediate application in the manufacture of semiconductor devices. These water quality requirements are documented in the ASTM specification D 5127-07, Standard Guide for Ultra Pure Water Used in the Electronics and Semiconductor Industry and SEMI F63-0309, Guide for Ultrapure Water used in Semiconductor Processing.

The method and apparatus of the instant invention operate pursuant to the discovery that particles, nano-particles, colloids, molecules, and ions in highly purified liquids typically exhibit a charge or charge polarity. It has been discovered that the majority of organic and inorganic constituents, of various sizes, in highly purified or ultra-pure water will exhibit a negative charge (electrical potential). For example, bacteria and organic molecules have a negative surface charge as a result of carboxyl and phosphate groups. The negative charge is stable over a wide pH range between 2 and 11. The negative charge has been verified by electrophoretic, isoelectric and colloid titration methods, and by the preferential absorption of anionic stains. In ionic-buffered aqueous solutions the magnitude of the negative charge can be reduced by the development of a positive ion counter-layer. However, since highly purified water is deionized, charged particles have a poorly developed counter-ion layer, thus enhancing the negative zeta potential.

Non-biological particles in highly purified water usually originate from system liners, resin beds (resin fragments), pipes, gaskets, and naturally occurring ionic species. A resin fragment exhibits a strong anionic or cationic charge characterized by its functional group. In highly purified water systems, piping and gasket materials are usually composed of chlorinated and fluorinated hydrocarbons, and/or stainless steel. Because of the natural hydrophobicity of negative charges in water, many nonorganic and non-polar materials collect negative charges from the surrounding water. Negative ions tend to be excluded from the bulk of the liquid and accumulate at interfaces between a particle and the water. As a result, even particles without active functional groups develop a net negative charge. Zeta-potential evaluation of deionized water and wafer-cleaning experiments support the theory that nano-particles found within ultra-pure water have a strong negative zeta-potential.

The further understanding of organic and inorganic charge characteristics and the prior art as described in Wildermuth, U.S. Pat. No. 5,128,043, incorporated herein by reference, has led to the novel method and apparatus of the present invention wherein both organic and inorganic constituents can be captured from highly purified liquids with imposition of an electromagnetic field such as a direct current (DC) electric field or a magnetic field. Although a DC electric field is presently preferred, the use of other fields is possible, and the device may even operate with AC excitation (dielectrophoretically) because of its coaxial cylindrical construction. The contamination can be mobilized within a weakly conductive dielectric, such as highly purified liquid, by an electrical field (E-field) force on particles, nano-particles, colloids, molecules, and ions, causing constituents to be captured and agglomerated on the anode and cathode electrodes. The prior Wildermuth patent described negative charges on particles and the mobilization/separation of charged particles within an electric field. Importantly, the present invention mobilizes, captures and agglomerates contamination at the electrodes. The present invention allows time for contamination to fully travel to the electrode, and at the electrode the electric field has sufficient energy to overcome Van der Waals Forces, permitting attachment and agglomeration of constituents to the electrode or to other attached organic and inorganic material. The captured and agglomerated particles can be later released under controlled conditions as part of water purification or analytical systems described below in detail.

The invention operates by establishing laminar flow of the liquid and passing it through an electromagnetic field, transverse to the direction of flow of liquid, to induce mobility of charged soluble and insoluble constituents in a desired and predictable direction transverse to the direction of flow.

The process initiates when high resistivity liquid is brought into one end of a cylindrical chamber through non-contaminating high-purity piping. Once the liquid enters the reaction chamber, design flow conditions (Reynolds Numbers less than 2,000) establish laminar flow. Preferably, the chamber has an aspect ratio (its distance dimension in the direction of flow (length) divided by its distance dimension transverse to the flow (diameter)) greater than 10:1, and more preferably greater than 20:1. Laminar flow is established within the chamber by allowing at least ten diameters upstream and at least five diameters downstream of a recovery zone in which capture of contaminants takes place. Utilizing laminar flow conditions to establish uniform flow lines (non-turbulent), an electromagnetic field is established in a cylindrical chamber by a medium voltage (less than 600 volts) DC potential, between a central, axially extending electrode (rod) and the wall of the chamber. Use of a voltage well below one kilovolt is believed to effectively eliminate mass migration off the electrodes and into the process liquid and render electrode insulation unnecessary. The DC electric potential is applied between the sidewall of the chamber and the rod such that either the chamber wall or the rod acts as a cathode and the other acts as an anode. As liquid flows longitudinally through the chamber, the electric field maintained transverse to the direction of laminar flow will produce a migration of the charged constituents toward the cathode or anode. At the cathode or anode, depending on polarity of charge, the constituent adheres and agglomerates on the electrode, thereby removing trace contaminates from the liquid. Purified liquid can then exit the chamber through a high purity piping system, similar to the chamber supply. Captured constituents can be released at will by reversing the polarity of the electrodes.

The above described process and apparatus have been developed into two systems, the first for the further purification of highly purified and ultra-pure water and the second for analytical sampling of highly purified and ultra-pure water.

The process and apparatus as described above removes contamination from highly purified liquids like ultra-pure water by capturing charged constituents on the center rod/electrode or cylinder wall/electrode, thereby purifying the water. In this embodiment (system), the contamination will be captured until one or both of the electrodes become saturated. At that point, or sooner, the device may be removed from service and the contamination released by reversing the polarity of the electrodes and discharging the contamination to waste. A series of polarity reversals, in combination with the forward turbulent flow of fluid, will release the contamination from the electrodes and prepare the apparatus for a new capture cycle, all without removing the device from the source of highly purified water. Importantly, the device can be configured to meet a variety of flow rate applications by scaling the design parameters associated with the current prototype and/or the parallel configuration of standard units.

In the preferred embodiments of the invention, no pre-charging of the feed stream is utilized. If desired, however, removal efficiency may be improved by pre-charging particles using chemical, ultraviolet, or electromagnetic energy to partially oxidize or charge-modify insoluble and soluble constituents.

The preferred method, apparatus, and systems will capture contamination for periods of days prior to becoming saturated, and then release concentrated and agglomerated contamination to waste, returning the apparatus to service in minutes. The removal efficiency may be varied by modifying design parameters that include detention time, cross-sectional area, electrode diameter and excitation.

The preferred device is simple, does not clog, requires little maintenance, can purge accumulated debris without disassembly, and does not require the use of contaminant-laden cleaning materials.

The method, apparatus and system easily handle large flow rates on the order of gallons (several liters) per minute, by scaling the design parameters and/or by providing parallel operation. Parallel devices will provide service and standby units, thereby maintaining continuous service.

The preferred device is compatible with ultra-pure water, does not deteriorate or contribute its own contaminants into the product water stream, and is not adversely affected by ozone, hydrolysis, or sharp-edged foreign matter. The preferred device does not provide bacterial colonization sites in contact with the process stream. The lack of colonization sites is associated with the configuration of the device, which preferably has a flow path free of square corners and which has a lethal E-field strength, and with the use of novel mechanical O-ring seals that eliminate cavities (dead legs) that could provide sites for bacterial colonization and contamination.

The preferred device is cost-effective to produce, operate and maintain and can be made of readily available materials that have been approved for use in high purity and ultra-pure systems. The preferred device uses the central electrode (rod) as a tensioning device to hold machined end blocks to the chamber tube. The assembly is inherently self-aligning and the rod is prevented from sagging.

Although the preferred and illustrative liquid is highly purified and ultra-pure water, the same methods, apparatus and system can be generally applied to devices designed to purify any highly purified liquids with a bulk resistivity greater than one megohm-centimeter.

It will be seen that the present device, system, and methods have several advantages over those disclosed in Wildermuth, U.S. Pat. No. 5,128,043.

The present invention does not segregate liquid streams into more purified and more contaminated streams, but rather captures particles on the electrode surface or surfaces, agglomerating them on the electrode or electrodes, and delivers a full stream of further purified water or other liquid. Therefore, the continuous waste stream of the prior device is eliminated.

Because the present device collects and holds contaminants, it permits the elimination of special structure to assure laminar flow all the way from the entrance to the exit of the device. Rather, the chamber itself may provide a removal zone within which contamination is moved to the electrodes. An entrance zone of the chamber itself may be long enough (about ten diameters) to establish laminar flow within the chamber ahead of the removal zone, and an exit zone may be long enough (about five diameters) to prevent disruption of laminar flow in the removal zone. Therefore, the reaction chamber of the preferred embodiments of the present invention lacks the baffles and multiple exits of the prior device and therefore greatly reduces the dead zones which may collect contamination such as bacteria. Further, the design permits entrance and exit of the liquid at angles to the axis of the device and permits smooth turns within the entrance and exit areas of the chamber. For these reasons, and because the periodic flushing cycles maintain the cleanliness of the interior of the chamber, the present device is also less susceptible to fouling and random release of contaminants and in illustrative embodiments can operate for a year or more without physically removing the device from the hydraulic circuit (process piping) to which it is attached.

In preferred embodiments, the device includes dielectric sleeves over the ends of the central electrode, beyond the removal zone, to extinguish the fringing electric field there and reduce or eliminate the resulting oxidation and stray contamination of the electrodes in the entrance zone and exit zone.

The present invention also is much smaller than the device of Wildermuth, U.S. Pat. No. 5,128,043. It is therefore easily installed at point-of-use locations, uses a much smaller power supply (typically 100 v to 150 v DC rather than 2,000 v to 3000 v DC), and uses far less power (on the order of 0.2 W rather than 90 W).

The same method and apparatus described above for removing contamination from highly purified and ultra-pure liquids such as water can be adapted for the analytical evaluation of highly purified and ultra-pure liquids such as water. A key advantage of this embodiment is the relatively high sampling rate and the agglomeration of contamination within the bulk liquid and/or at the electrodes. Highly purified or ultra-pure water contains only trace amounts of soluble and insoluble constituents such as particles, nano-particles, colloids, molecules, and ions. As a result, contamination is poorly detected by on-line OPCs with a small sample volume and a detection limit of 40 nm. As an alternative to OPC, filter membrane sampling takes a large volume of water and a significant amount of time (weeks) to collect enough particles for standard SEM/EDS evaluation.

The analytical system of the present invention samples water at a rate of greater than 300 ml/min compared to 50 to 100 ml/min for currently available procedures. Equally important, the contamination that is collected on the electrodes agglomerates or combines into larger particles which are more effectively detected by OCP and SEM instrumentation, thereby detecting smaller particles than the existing analytical devices for highly purified or ultra-pure water. As a result, the useful concentration of particles is collected in days versus weeks. The analytical embodiment therefore provides more timely process control and system upset evaluation of highly purified and ultra-pure water systems.

The analytical embodiment captures and agglomerates particles on the cathode and anode electrodes. After a period of time that is dependent on the quality of water (concentration of contamination), the polarity of the electrodes is reversed multiple times to release contamination from the electrodes and to allow the concentrated waste stream to be directed to a standard 50, 100, or 200 nm sample membrane. The concentrated and agglomerated particles can be counted and sized by an OPC or counted, sized, and elementally evaluated by SEM/EDS. Once the contamination has been collected on the sample membrane, the device can be flushed and returned to service for a new capture cycle.

The analytical embodiment provides a method, apparatus, and system capable of capturing a wide range of soluble and insoluble contamination on anode and cathode electrodes and then releases agglomerated contamination that is large enough to be evaluated by existing OPC and SEM/EDS analytical technologies.

Utilizing variable removal efficiency by adjusting operating parameters, such as interelectrode voltage and flow rate, allows the segregation and identification of specific contamination based on charge characteristics (mobility).

In some cases it is desirable to initiate a capture cycle on receipt of an external signal that an upset has occurred in the liquid system being analyzed. This assists in identifying only contamination that may result from the upset. The present system provides that capability.

The operation of the contaminant-removing apparatus, the purifying system, and the analysis system may all be controlled by automated controllers. Thus, timed capture, release/self-cleaning, powered and unpowered flushing, electrode shorting, signaling external monitoring equipment, and data logging may all be performed by commercially available programmable logic controllers and associated A/D converters that control excitation frequency, duration, and amplitude, and that control valves, relays, signaling, and triggering. The systems may thus be provided as turnkey integrated, portable systems capable of unattended operation over weeks at a time. Automating the device and systems has been found to greatly enhance the performance of the systems and the reproducibility of results.

Current flow and voltage (or power consumption) may be monitored during capture mode by the contaminant-removing device as an indication of the amount of contamination in the highly purified liquid; likewise, readings from contaminant-measuring equipment during release mode may be monitored and fed back to the control system and may control such variables as excitation amplitude and polarity and valve timing in a closed-loop control system as opposed to an open loop system operating in scheduled time sequences.

Although purification and analysis systems are described as individual systems optimized for those functions, it will be understood that contaminants from the self-cleaning mode of the purifying device may be captured and analyzed, and that the further-purified liquids from the analysis system may be utilized in an industrial process.

BEST MODES FOR CARRYING OUT THE INVENTION

Figure 1:
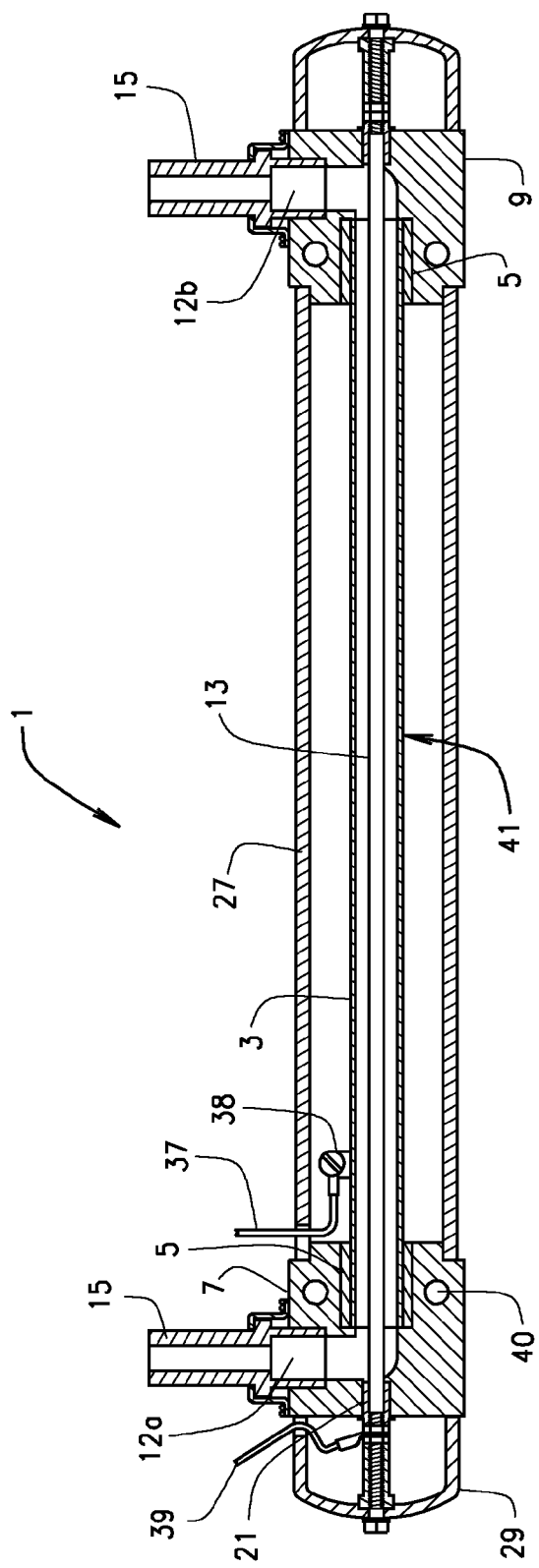
FIG. 1 is a cross-sectional view of a reaction chamber in accordance with the present invention, illustrating the components and device assembly.

The invention comprises, among other things, a system for purifying already highly purified or liquids such as ultrapure water, a system for analyzing impurities in such liquids, methods of using these systems, and a reaction chamber useful in both systems.

Highly purified or ultra-pure water, having a bulk resistivity in excess of one megohm, is made by conditioning/treating naturally occurring well or surface water with a series of unit processes that remove suspended and dissolved constituents. These unit processes usually include, but are not limited to, settling, coagulation, clarification, softening, flotation, depth filtration, membrane filtration, absorption, degasification, temperature adjustment (heat exchanger), reverse osmosis, distillation, ionic exchange, oxidation, disinfection and ultrafiltration. These treatment steps progressively purify water by removing suspended and dissolved constituents. The selection and arrangement of unit processes is determined by the quantity of specific constituents, unit process performance, arrangement of unit processes, and the final water quality requirements. Final water quality requirements are determined by manufacturing requirements and vary slightly among the semiconductor, pharmaceutical, photovoltaic, metal plating, and power industries. The slight variation is caused by the impact of specific constituents. For example, the pharmaceutical industry is very concerned about trace quantities of bacteria. On the other hand, the power industry is concerned about trace quantities of inorganic contamination. Importantly, the present process, apparatus, and system are effective at removing trace amounts of organic and inorganic contamination and will find application in any industry where small amounts of contamination need to be removed or measured for the effective operation of a highly purified and ultra-pure water system.

A. Reaction Chamber and Method of Operation

A central element of this invention is the reaction chamber where soluble and insoluble constituents are captured from highly purified liquids such as ultra-pure water. If one skilled in the art, as described in the previously-mentioned Wildermuth, U.S. Pat. No. 5,128,043 A1, treats purified, weakly-conductive liquids with an electromagnetic field, the field can steer charged soluble and insoluble contamination through the liquid using the same physical principle as for that of an evacuated cathode ray tube where the field steers a moving electron beam. As previously noted, the majority of contamination within highly purified and ultra-pure liquids comprises negatively charged particles, nano-particles, colloids, molecules, and ions.

Although not presently preferred, charge-neutral contaminants in the liquid can be pre-charged prior to entry into this process by a suitable charging device upstream of the reaction chamber. The pre-charging can be accomplished by partially oxidizing the constituents. Partial oxidation can be accomplished by exposing the constituents to ultraviolet (UV) radiation or chemical oxidation by oxidizers like, but not limited to, ozone and hydrogen peroxide. Alternatively, passing the constituents through an appropriately configured electrical field can also charge-modify or polarize charges on particles or constituents. The pre-charging or charge polarization of particles could easily be incorporated into the purification or analytical systems to further enhance the capture efficiency or could be added to systems treating liquids with a large concentration of charge-neutral particles, nano-particles, colloids, molecules or ions.

Figure 2:
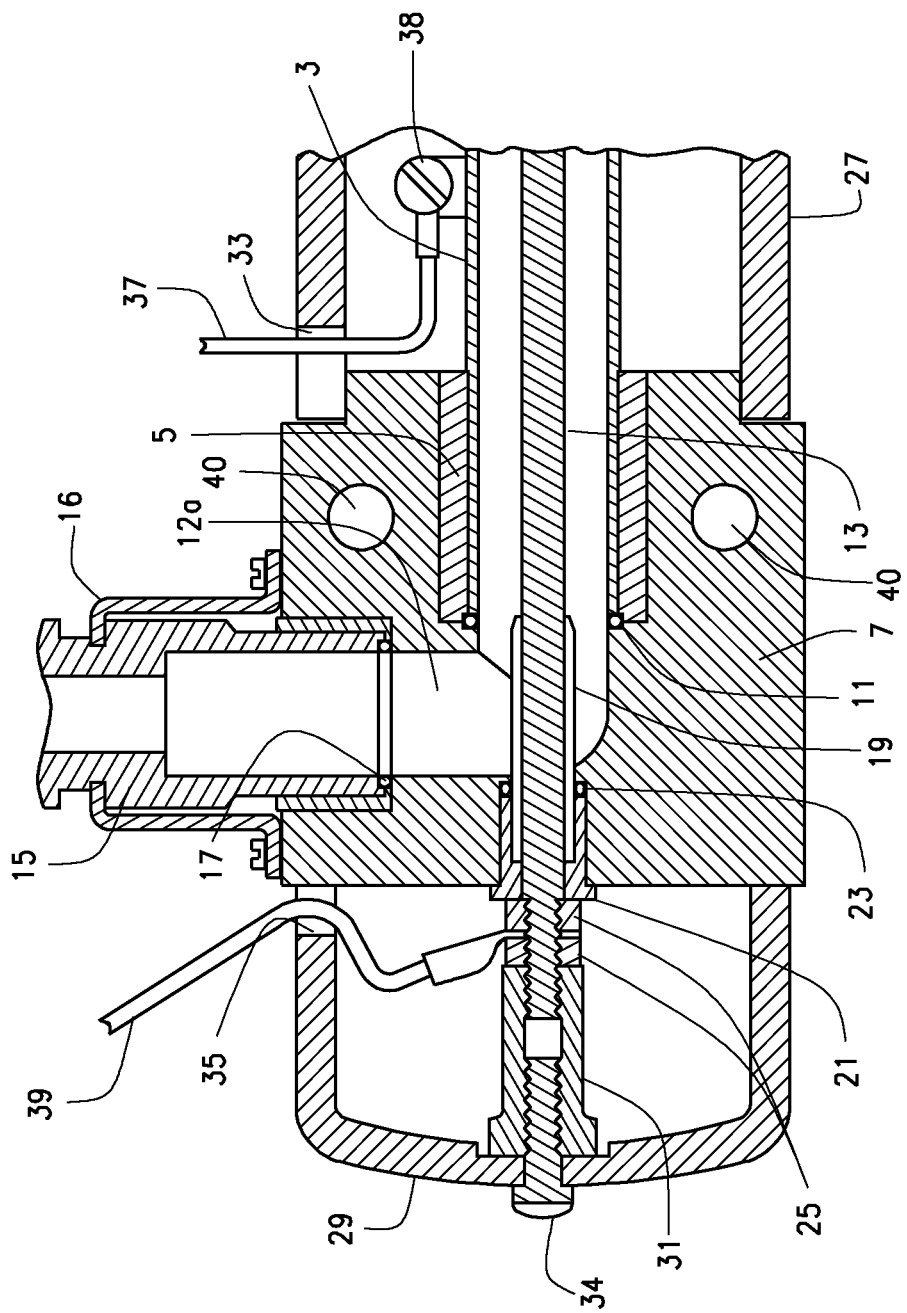
FIG. 2 is a detail of one end portion of the reaction chamber of FIG. 1, the other end portion being a mirror image thereof.

Referring now to the drawings, and in particular to FIGS. 1 and 2, a reaction chamber 1 of the present invention incorporates some of the insights of the aforesaid Wildermuth patent but improves on that device. The chamber design and fabrication does not contribute contamination to the high purity liquid or ultra-pure water.

The reaction chamber 1 includes a tube or cylinder 3 made of 316L stainless steel with a Ra finish of less than 5.0. The tube 3 is 16-inches (40.64 cm) long, with an external diameter of 0.75-inches (19.05 mm) and an internal diameter of 0.625-inches (15.875 mm). The ends of the tube 3 have 316L stainless steel collars 5 pressed onto them. Inlet block 7 and outlet block 9 are sealed to the ends of the tube 3 and collars 5 by O-rings 11. These blocks are either machined or molded polyfluorocarbon, such as ethylene chlorotrifluoroethylene (ECTFE; e.g., Solvay Solexis HALAR®) or polyvinylidene fluoride (PVDF; e.g., Solvay Solexis HYLAR®). They are designed to direct the incoming or exit flow in or out of the reaction chamber. The radius of the inlet passage 12a and outlet passage 12b in these blocks is a sweeping 90-degree elbow to encourage laminar flow, although true laminar flow is not achieved until well into the tube 3 as described hereinafter. The blocks 7 and 9 are also used to align and position the tube 3 and a coaxial central rod electrode 13 for proper operation. Polyfluorocarbon port adapters 15 are fitted into the block inlet 12a and block outlet 12b of the blocks 7 and 9, respectively, and sealed with O-rings 17. Mechanical retainers 16 on the outer shoulders of adapters 15 compress the O-rings 17 and prevent liquid pressure from ejecting the adapters from the blocks.

Center electrode/rod 13 is made of 316L stainless steel with a Ra finish of less than 5.0. It has a length of 19.9-inches (50.5 cm) and a diameter of 0.188-inches (4.775 mm). The rod 13 has insulative PVDF sleeves 19 which extend from the mouths of the tube 3 outward across the inlet and outlet passages to limit E-field fringing and oxide buildup in those areas. The sleeves 19 have an inner diameter slightly less than the rod 13 and form a tight, waterproof fit over the rod 13. The outer ends of the sleeves 19 slip into O-ring packing glands 21 which extend into the blocks 7 and 9 from outside the blocks and form a seal with O-rings 23. The rod 13 is threaded on both ends. Nuts 25 are threaded onto the rod 13 in order to assemble the components and compress O-ring seals 11 and 23.

The outer tube 3 is typically the cathode (negative charge) and the center electrode 13 is typically the anode (positive charge).

The tube 3 is preferably covered with an insulative housing 27 in the form of a 2-inch (5.1 cm) PVDF tube trapped between the blocks 7 and 9. This plastic tube forms a protective housing designed to electrically isolate the outer electrode 3 from contact for safe operation.

Protective end caps 29 are molded of insulative material such as PVDF. These plastic caps are designed to electrically isolate the inner electrode 13 from contact for safe operation. An insulator such as polyimide adapter 31 is threaded onto the end of rod 13, and a fillister head cap screw 34 is threaded into the insulative adapter 31.

Holes 33 and 35 may be provided in the insulative housing 27 and one of the end caps 29, respectively, for electrical lead 37 to the contact 38 on tube 3 and electrical lead 39 trapped between nuts 25 on rod 13.

Four mounting holes 40 are illustratively drilled through the blocks 7 and 9.

As will become apparent later, the primary deposition and agglomeration of particles will take place in a central removal zone 41 of the reaction chamber 1, extending about 6-inches (16 cm) from the inlet end of the tube 3 to about 3-inches (8 cm) from its outlet. This is the area in which flow in the tube has become laminar.

The O-ring seals for sealing the rod 13 and cylinder 3 to the inlet/outlet blocks 7 and 9 and for sealing the inlet and outlet adapters to the blocks are made of EPDM. The O-rings, particularly the cylinder and adapter O-rings, are a unique design to minimize contamination during operation.

Figure 3:
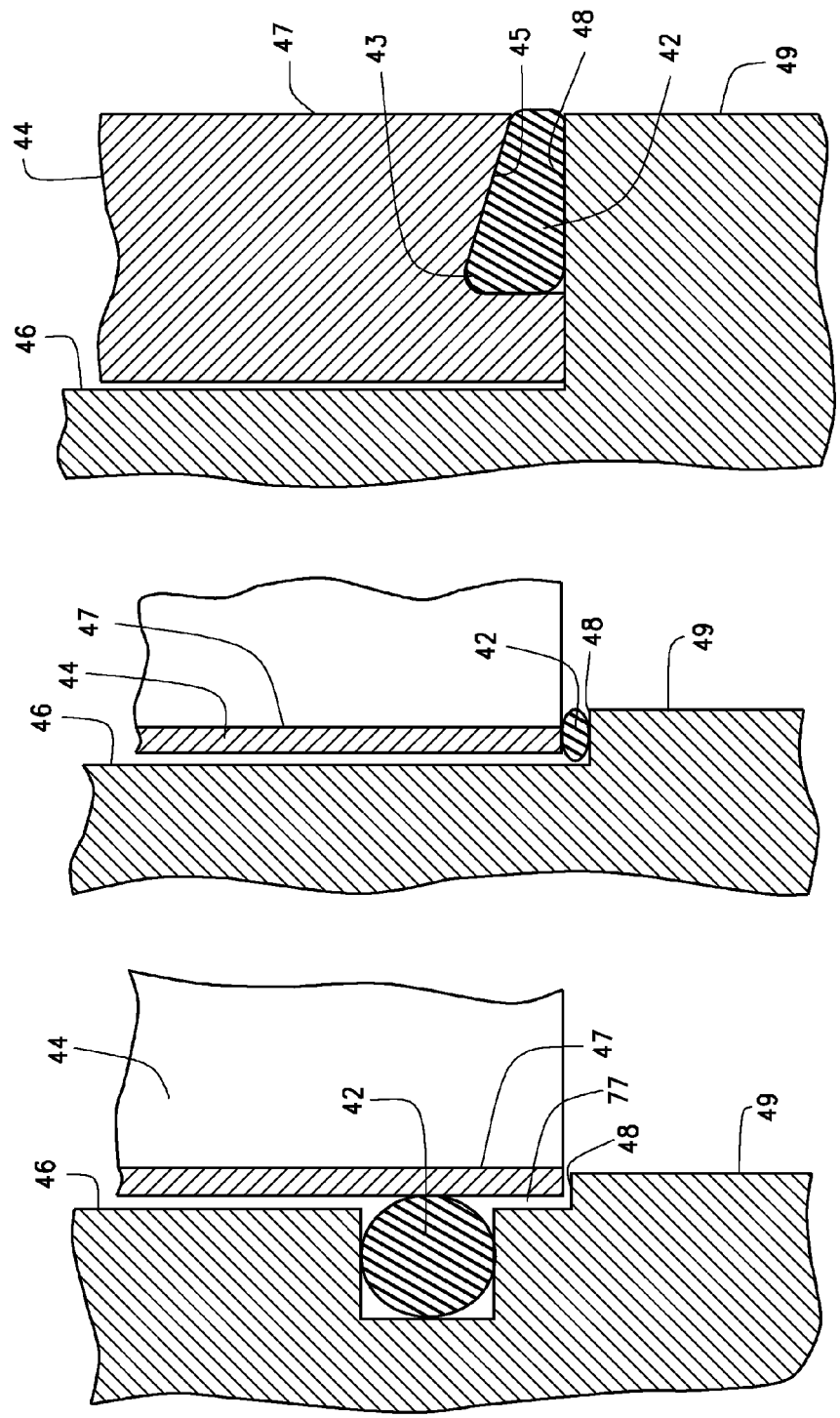
FIGS. 3A and 3B are detail drawings of two prior art designs for sealing components in hydraulic systems.
FIG. 3C is a detail drawing of a new design approach for sealing components in hydraulic systems, using a specially designed trapezoidal O-ring groove to provide a low contamination seal in the reaction chamber.

FIGS. 3A and 3B illustrate existing designs of O-ring joints. FIG. 3A's design compresses an O-ring 42 between the exterior of a tube 44 and the interior of a socket 46 into which the tube is pushed. It will provide leak protection. However, the design causes a small gap or "dead leg" 77 to form between the exterior of the tube 44 and the interior of the socket 46. The gap creates an environment for the growth of bacteria that will contaminate the liquid to be purified or measured. FIG. 3B's design will also provide an effective seal and will reduce dead leg volume. However, as the O-ring 42 is compressed, it will expand into the flow line of the chamber. Once an O-ring protrudes into the flow line, it can be chemically attacked or mechanically eroded and deteriorate, causing the release of particles into the highly purified liquid. In contrast, the design of the present invention shown in FIG. 3C does not have gaps or protruding O-rings. In this new design, as the O-ring 42 is compressed, it fills a specially designed O-ring groove to seal without a gap or protrusion. The groove 43 is formed to be deeper away from the liquid it is sealing than at the liquid interface. One side face of the groove 43 is formed by an interior annular rabbet 45 in the end of the tube 44 being sealed, and the other side face of the groove 43 by the bottom 48 of the socket 46 into which the tube is pushed. The rabbet 45 is sized to allow the O-ring 42 to compress into the larger radially outer portion of the groove 43, while leaving the interior face of the compressed O-ring 42 substantially flush with the interior bore 47 of the tube 44 and the fluid-flow passage bore 49 of the socket 46. The rabbet 45 preferably forms an angle of about 290°±5° with the interior of the tube 44 (i.e., 20°±5° from the plane of the end of the tube 44). Preferably, the O-ring is placed in the rabbet 45, and the tube 44 pushed into the socket 46 until the radially outer part of the end of the tube abuts the bottom 48 of the socket 46. As a result, the two surfaces are sealed without potential contamination of the highly purified liquid. It will be understood that the rabbet could be provided in the bottom of the socket 46 rather than in the end of the tube 44. The design of FIG. 3C is preferably used for O-rings 11 and 17 of the illustrative embodiment of FIGS. 1 and 2.

Figure 4:
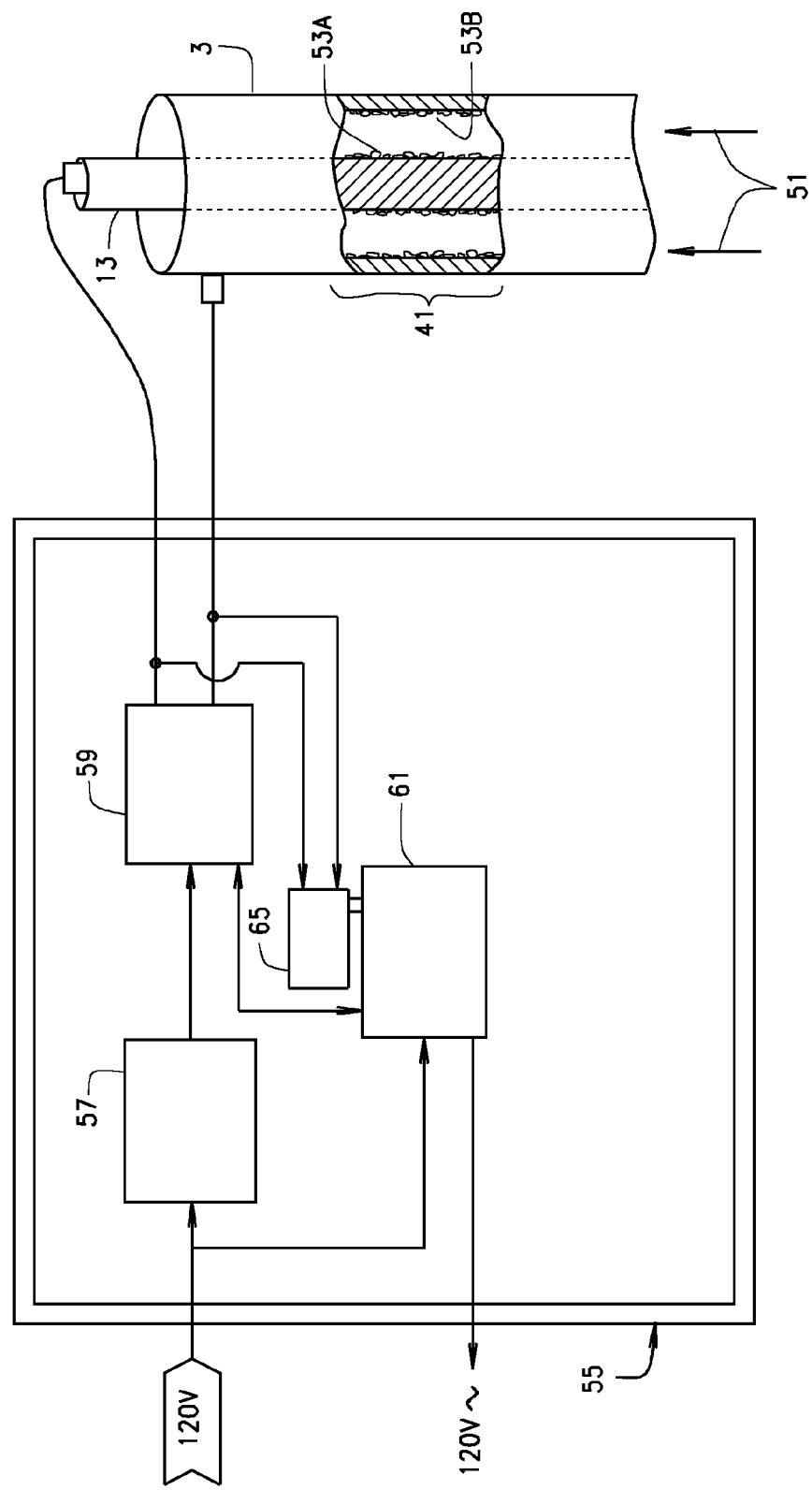
FIG. 4 is a schematic diagram illustrating electrical system components used to power the apparatus and control the liquid purification and analytical systems.

FIG. 4 schematically illustrates the control of electrical power to the reaction chamber 1. In FIG. 4, highly purified or ultra-pure liquids 51 with trace amounts of contamination enter the removal zone 41 of the cylinder 3 under laminar flow conditions. Once in the cylinder removal zone 41, the contamination will move radially to the surface of the center rod (inner electrode) 13 or to the inner wall of the cylinder (outer electrode) 3. Finally, purified water will exit the cylinder. The accumulated material 53A and 53B on the inner and outer electrode, respectively, can be removed by reversing the polarity, causing the accumulated and agglomerated material to exit the cylinder. The electric field and switching are controlled by a power and control box 55 which illustratively takes incoming alternating current power into an AC-to-DC power supply 57 which feeds switching circuits 59. The switching circuits 59 are controlled by a programmable logic controller 61. The switching circuits 59, under the control of the logic controller 61 control the polarity of power applied to the tube 3 and rod 13, as well as the amount of power and the timing of changes in the polarity of power applied to the tube 3 and rod 13.

Figure 5:
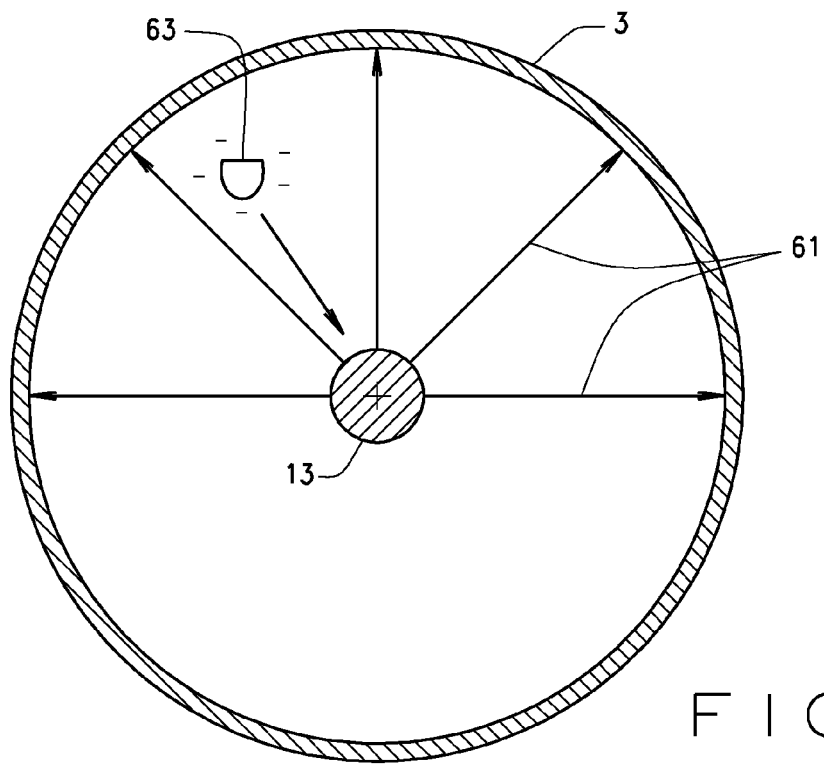
FIG. 5 is a schematic diagram illustrating the electromagnetic field that induces mobility of charged soluble and insoluble constituents within the reaction chamber.

As shown diagrammatically in FIG. 5, the apparatus operates on the principle of electromagnetic field-based attraction/repulsion of electrically charged material. As used herein, the term "electromagnetic field" includes fields produced by a static or dynamic electric field, or by a static or dynamic magnetic field or by a combination of any or all of these. The reaction chamber wall 3 acts as one electrode, in conjunction with the interior rod electrode 13. High resistivity liquid is brought into one axial end of the cylinder through non-contaminating high-purity piping. Once the liquid enters the reaction chamber, design flow conditions (Reynolds Numbers less than 2,000) establish laminar flow. Utilizing laminar flow conditions to establish uniform flow lines (non-turbulent), an electromagnetic field E having field lines 61 is established in the cylindrical chamber by a medium DC voltage (less than 600 volts), between a central axially extending electrode 13 and the wall of the chamber 3. DC electric potential is provided between the sidewall of the chamber 3 and the rod 13 such that either the chamber wall or the rod acts as a cathode while the other acts as anode. As the liquid flows longitudinally through the chamber, the electric field maintained transverse to the direction of laminar flow allows for the migration of the charged constituents 63 having charge q toward the cathode or anode. At the cathode or anode, the contamination adheres and agglomerates on the electrode, thereby removing soluble and insoluble contaminates. Purified liquid can then exit the chamber through a high purity piping system, similar to the chamber supply piping. The requirement that the soluble and insoluble contamination be able to traverse the chamber before the liquid leaves the chamber can be met by controlling the following variables:

1) Flow rate—slow the flow of the liquid (even to a stop).
2) Field strength—increase the field strength to move the charged species faster.
3) Aspect ratio—increase the aspect ratio of the chamber. The illustrative apparatus uses an aspect ratio of approximately 24:1.

During the separation process, soluble and insoluble material is captured and/or agglomerated into larger particles. Based on the understanding that the majority of particles, nano-particles, colloids, molecules, and ions have negative charges, it is optimum to establish the center rod as the anode and the cylinder as the cathode as shown in FIG. 5. The concentrating and agglomerating of contamination are key discoveries that allow the invention to exceed currently available technologies for both the water purification and analytical applications.

Continuing to refer to FIG. 5, because of the coaxial-cylindrical electrode geometry, E-field forces move the charged constituents radially in the chamber, separating the contamination from the bulk fluid. The basic physical equation of the positioning force is:

$$F = qE$$

where:
F is the vector quantity of force developed, in mks units.
E is the vector quantity of E-field strength.
q is net charge on the charged species acted on by the E-field.

In short, this relationship states that the magnitude of the force on any charged particle 63 is a product of its net charge and E-field strength. Its direction is parallel to the E-field direction at that location in the chamber, and the product sign will be negative if the force acts opposite to the direction of the E-field (i.e., if the net charge is negative).

The E-field equation for the chamber away from either end will be recognized as the E-field for a cylindrical coaxial capacitor in the equation:

$$E = (V/[r^* \ln(b/a)]) a_r \text{ (for } r \text{ between } a \text{ and } b\text{)}$$

where:
V is the potential difference (voltage) between the electrodes.
r is the distance (the independent variable) measured in meters from the center of the cylinder
b is the value of r at the inside wall of the chamber shell.
a is the value of r at the outer diameter of the central rod.
$a_r$ is the unit vector showing field direction.

This equation applies only to the fluid volume inside the chamber, per Gauss' Law, where no E-field can exist inside the central rod or outside the coaxial capacitor-like chamber The equation states that E-field forces on charged particles, nano-particles, colloids, molecules and ions; (1) have only radial components, (2) are directly proportional to applied voltage, and (3) are inversely proportional to radial distance from center by a constant determined by radial chamber dimensions. The systems have been operated with field strengths ranging in magnitude from 5,300 to 70,000 V/m.

The magnitude of field strength is a function of radial distance from the center of the chamber. It may be noted that the field magnitude is zero both inside the center electrode and beyond the inner diameter of the cylinder. The nonlinear increase in E-field strength near the inner electrode is novel to the chamber design and makes a significant contribution to the removal efficiency of the chamber design. This will be discussed in more detail below.

Since the chamber is not of infinite length, some fringing would normally occur at the ends. This would not negatively impact the operation of the device; at the entry end, no separation has yet occurred, and at the exit end, the contamination has already reached the specified electrode. Finally, fringed E-field lines still apply force to the charged constituents in such a way that they would arrive at the intended destination, albeit by paths bowed in the longitudinal direction. In order to minimize oxide buildup in the fringing area, an insulative sleeve 19 has been installed on the center electrode (rod) at the entrance and exit to the reaction chamber. The sleeves are approximately one inch (2.5 cm) in length and essentially extinguish the field in the fringing areas between the tube ends and the entry points of the rod into the end blocks.

Other forces are present in the chamber, but their magnitude relative to the E-field hydrodynamic forces are so small that they can be ignored in the chamber analysis. For example, gravitational and buoyant forces can be dismissed because the soluble and insoluble constituents have a very low specific gravity or are soluble within the aqueous environment. Magnetic field forces are present due to the current flowing in the electrode and in the fluid. However, the magnetic fields set up by the current through the fluid are vectorially self-cancelling, and the worst case magnitude of the forces set up by electrode current magnetic fields is about $10^{-8}$ less than those due to the E-field.

Figure 6:
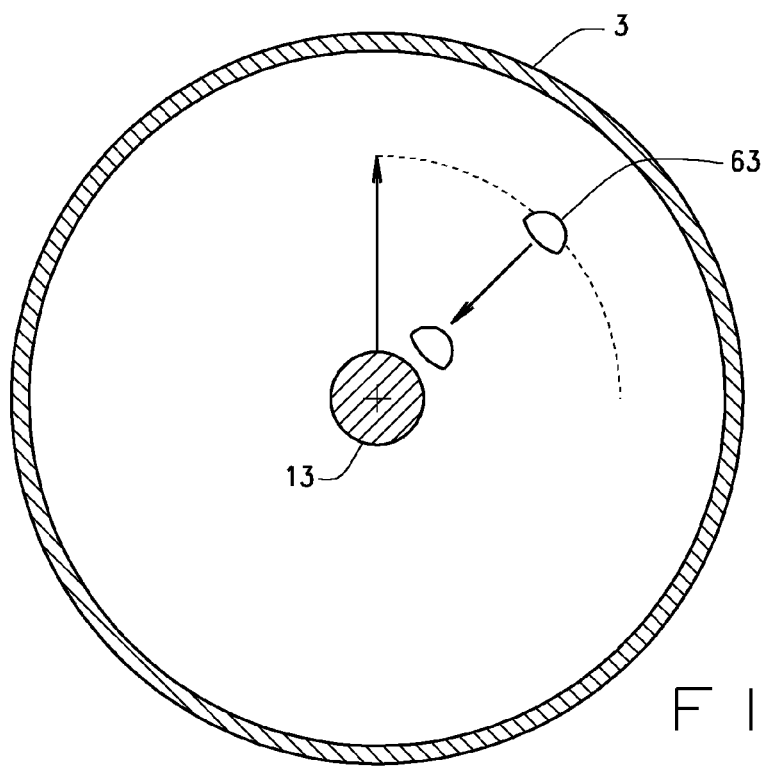
FIG. 6 is a schematic diagram illustrating the impact of the laminar flow and coaxial-cylindrical design on the movement of constituents within the reaction chamber.

The hydraulic design of the reaction chamber 1 is shown diagrammatically in FIG. 6. The cylindrical geometry of the chamber enhances separation efficiency over rectangular and other cross-sectional designs. This is due to inherent advantages in the E-field and volumetric geometries used in this application. Specifically, the electrical field magnitude increases non-linearly, rising at an ever-increasing rate when moving from the cylinder electrode 3 of the chamber to the inner (rod) electrode 13.

In addition, by definition, volumetric concentration (e.g. particles/liter) has the volume term in the denominator. Therefore, when the particle 63 is moving from the outer electrode to the inner electrode, the effective concentration per longitudinal axis unit length increases at an increasing rate. To be exact, the volume per unit length of the chamber is derived from the equation for the difference in volumes of right circular cylinders of length L and radii r and $r_a$:

$$\text{Volume} = L \times \pi \times (r^2 - r_a^2)$$

or by manipulation $$\text{Volume}/L = \pi \times (r^2 - r_a^2) \text{ (where } r_a \text{ is less than } r\text{)}$$

This equation states that the volume per unit length of the chamber at a particular distance from the outer surface of the rod is proportional to the difference between the squares of the radial distances outward from the rod and the rod radius. This means that as charged constituents move closer to the inner electrode, the concentration (i.e., quantity per unit volume) increases by the inverse of the difference between these squares.

Both the non-linear field strength and the decreasing cross-sectional area are key elements to defining the rod electrode as the anode, thus attracting the majority of constituents, which are carrying a negative charge. In effect, this maximizes field strength in an area where the contaminant concentration is highest, improving efficiency of the device. If the liquid has unique characteristics where the majority of the particles are positive, then the polarity can be reversed to more efficiently remove positively charged constituents.

Referring again to FIG. 4, the E-field discussed above can be established by applying DC voltage across the chamber wall and rod. This E-field is generated, controlled, and monitored by components located within an electrical power and control box 55. The electrical power and control box receives 120 VAC for the power supply 57 and the programmable logic control (PLC) 61.

The power supply converts the 120 VAC to fully rectified and filtered (<10% ripple) DC power used in the reaction chamber. The DC power can be adjusted between 0 and 600 VDC for the capture and release cycles. For the configuration above, the capture voltage between 75 and 150 VDC and release voltage, typically 150% of the capture voltage, worked satisfactorily. As shown in FIG. 4, the DC output from the power supply is directed to switching logic circuits 59, where the DC power to the reaction chamber is controlled by a group of relays. The relays, controlled by the PLC 61, determine the application of capture or release voltage, the polarity of the rod/cylinder electrodes, and the sequencing and timing of capture and release cycles, and electrically short circuit the electrodes together whenever electrode excitation is not applied.

As shown in FIG. 4, the relays control DC power to the reaction chamber, with one lead terminating on the center rod electrode 13 and one lead terminating on the cylinder electrode 3. As shown in FIG. 5 and as described above, the E-field will mobilize, agglomerate and attach contamination at the electrodes. The contamination can be removed from the electrodes by switching the relays to reverse the rod/cylinder polarity and boosting the voltage to the release level.

The controller or PLC 61 is programmed to automate the switching of the relays, operate the solenoid valves as described below with respect to FIGS. 8 and 9, and monitor key operating voltage and current parameters. For the operation of the water purification or analytical systems, the PLC can be programmed to automate and sequence the power and hydraulic operations to achieve repeatable and reliable operation. The PLC 61 collects operating data, including interelectrode voltage and current, via an analog-to-digital converter 65.

Figure 7A:
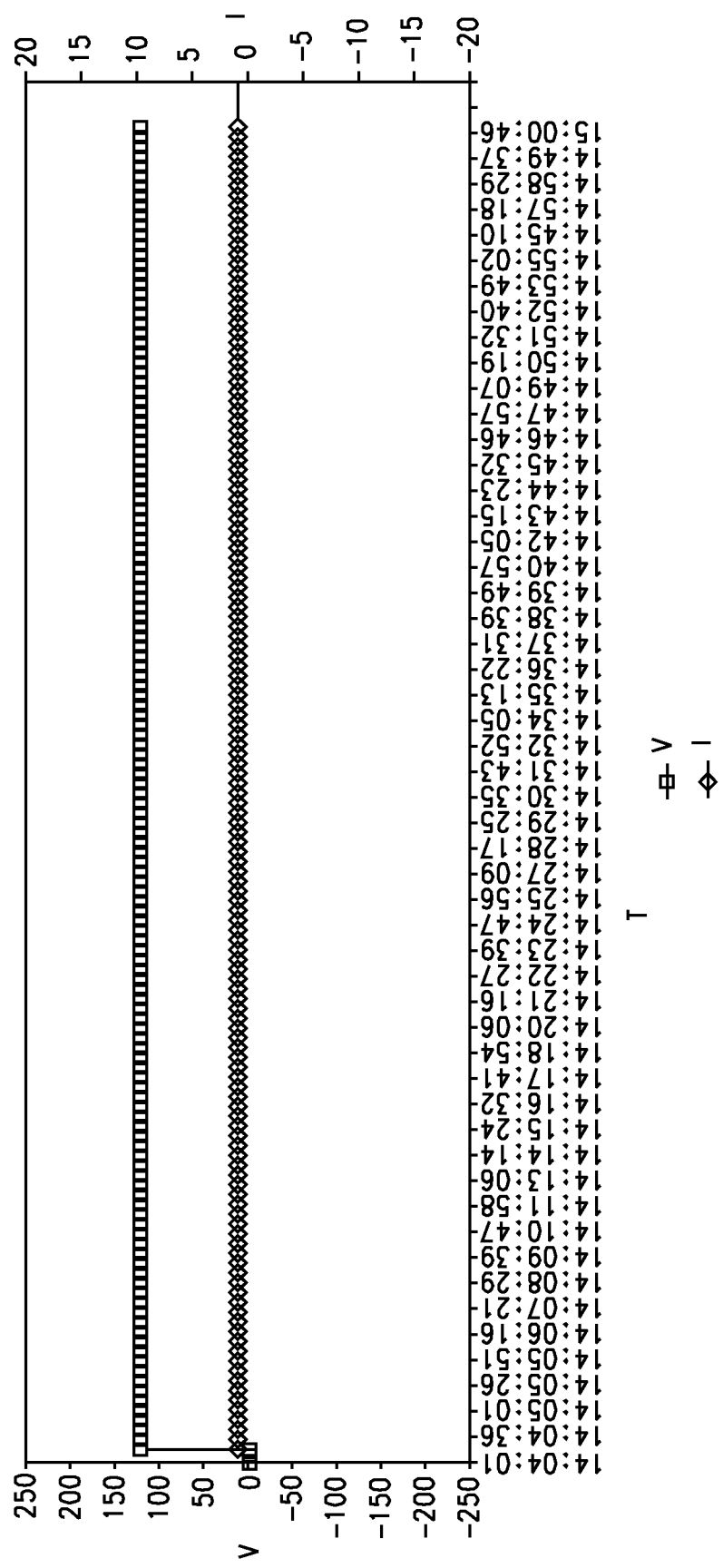
FIG. 7A is a graph illustrating typical reaction chamber voltage and current during the capture of soluble and insoluble constituents.
Figure 7B:
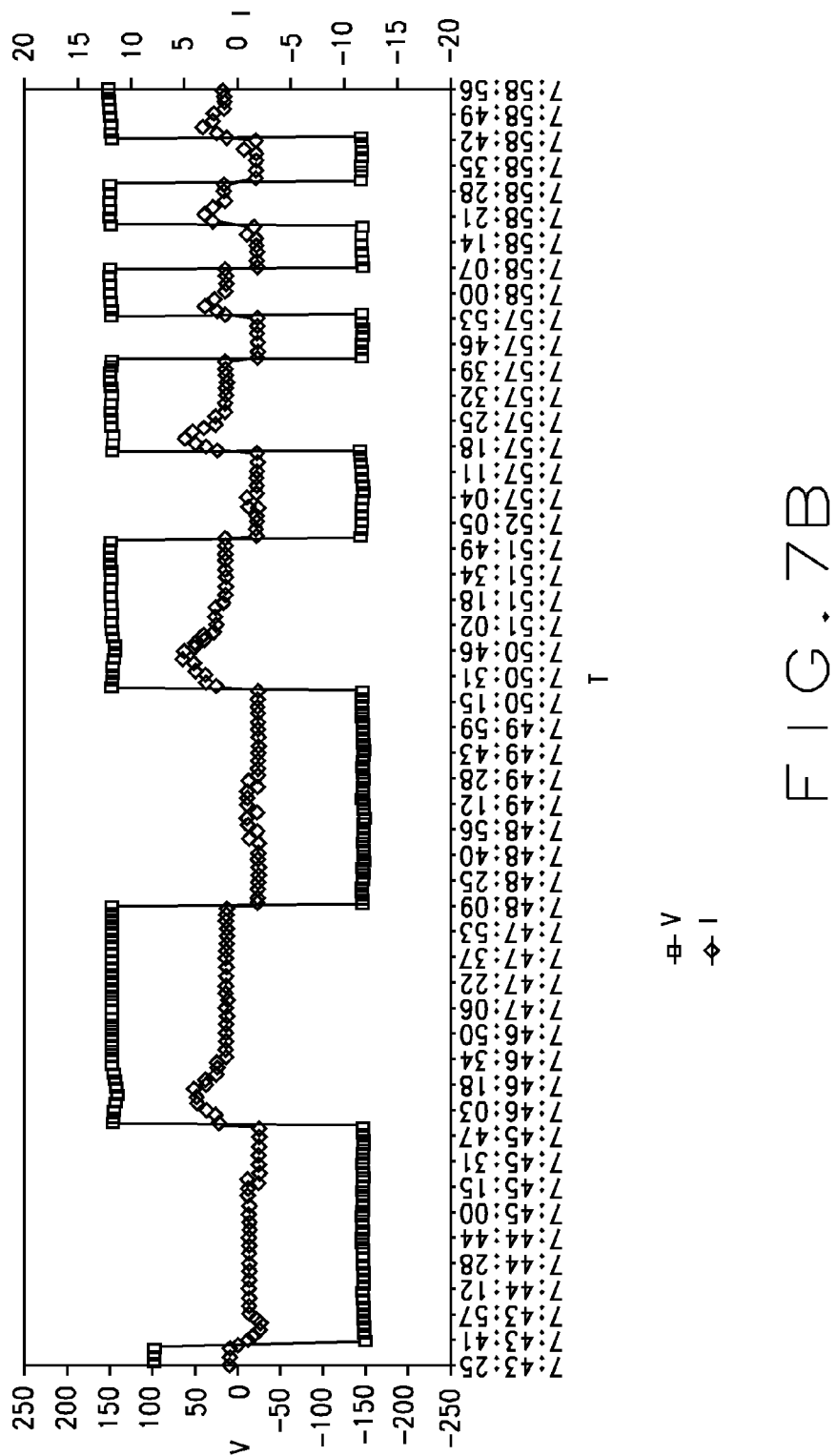
FIG. 7B is a graph illustrating typical reaction chamber voltage and current during the release of soluble and insoluble constituents.

The PLC 61 monitors and electronically stores the reaction chamber voltage and current from the analog-to-digital converter 65 during all cycles. FIG. 7A is a graph showing a typical DC excitation of the reaction chamber interelectrode voltage and current during a capture cycle at approximately 125 VDC, producing a current of 2 mA. For the configuration described above, this is typical for the purification and analytical systems during the capture of contamination from highly purified and ultra-pure water. FIG. 7B shows typical interelectrode voltage and output current during the release of particles from the reaction chamber. In FIG. 7B, the polarity of the DC field is switched every minute (6-times) and then every 30 seconds (6-times). As the polarity is reversed, one can observe the slight increase in current. The increase in the current is associated with the release of attached and agglomerated particles. As particles are released from the electrodes, their charges are available to transfer electrons and increase the current flow. It should be noted that these voltage/current profiles, being representative of contamination level, can be used to estimate the contamination level during operation and thus used to control the operation parameters, such as length of release cycles, etc. In addition, these voltage/current profiles, being representative of contamination level, can be used to directly report the contamination within the water being purified or analytically evaluated. The voltage/current graphs are representative of both the purification and analytical devices.

It will be seen the physical and electrical parameters of the preferred embodiment allow time for contamination to fully travel to the electrode, and at the electrode the electric field has sufficient energy to overcome Van der Waals Forces, permitting attachment and agglomeration of constituents to the electrode or to other organic and inorganic material attached to the electrode. It will also be seen that the release cycle permits substantially complete release of particles and agglomerations of particles from the electrodes of the device.

B. Water Purification System—Design and Operation

Figure 8:
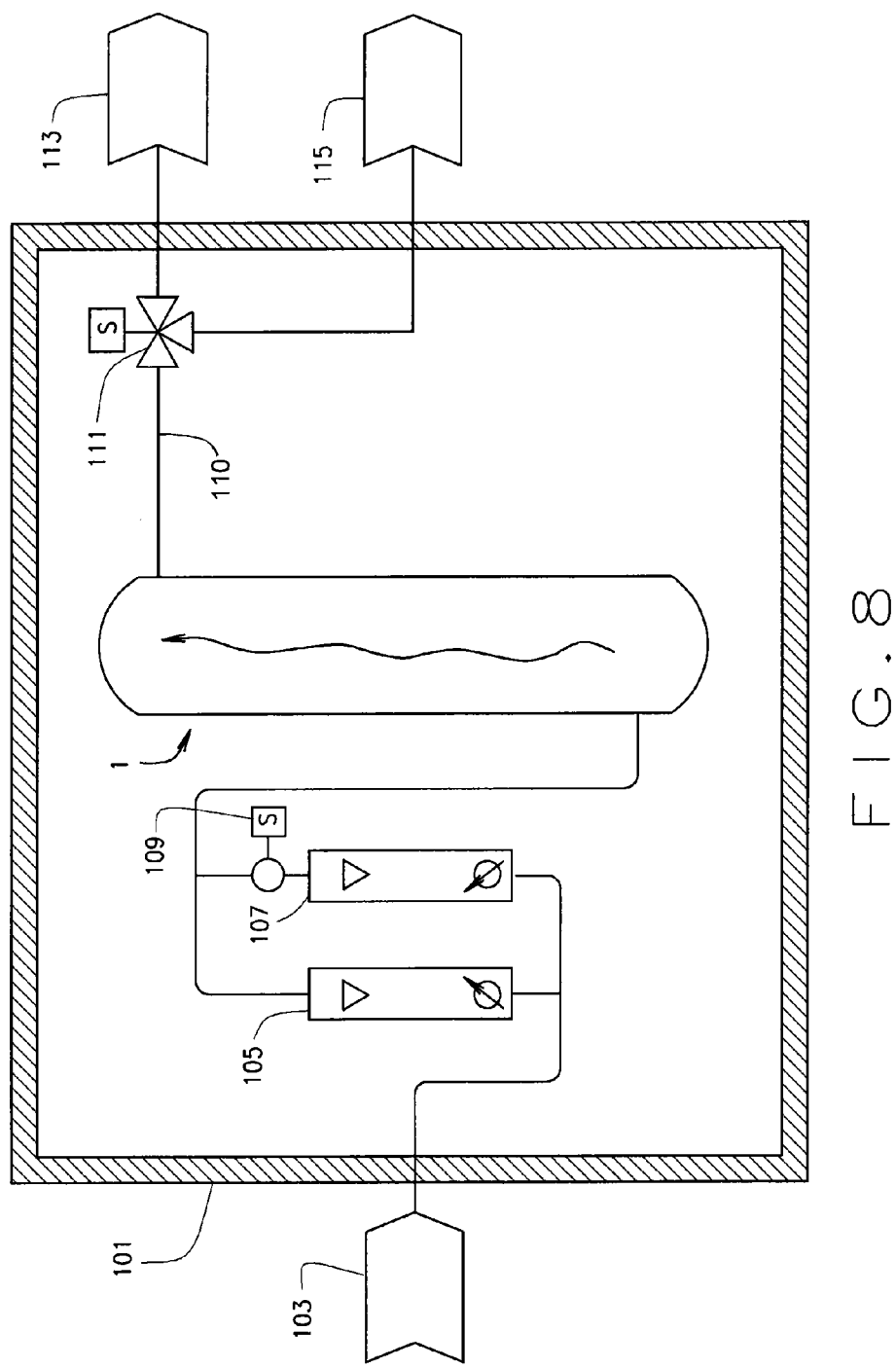
FIG. 8 is a schematic diagram illustrating the apparatus and the hydraulic components of one embodiment of system for further purification of highly purified and ultra-pure water.

Referring now to FIG. 8, a schematic of the hydraulic components located within the hydraulic component box 101 that works in conjunction with an electrical power and control box. The piping and component layout is a close representation of the system design, with the box orientated in the vertical position (top of the figure is up). All wetted surfaces associated with the tubing, fittings and system components are preferably made from fluoropolymers such as polyvinylidene fluoride (PVDF; e.g., Solvay Solexis HYLAR®) or polytetrafluoroethylene (PTFE; e.g. DuPont TEFLON®) high purity materials so as not to add any contamination to the in-coming water. Except for the reaction chamber, all components are available as standard parts from high purity water piping suppliers.

At the entrance 103, the highly purified or ultra-pure water described above enters the hydraulic component box. The inlet water pressure and temperature will be determined by the process requirements downstream of the device. Typical process requirements for manufacturing equipment are for a pressure between 20 and 80 pounds per square inch gauge (PSIG) (138 to 552 kPa) and between 1 and 90 degrees C. The apparatus has negligible impact on pressure (less than 1 PSIG (7 kPa) pressure drop) or temperature. As a result, the invention can be easily added to the existing water treatment systems without impacting existing pressure or temperature specifications. Alternatively, ultrafilters and membrane filters, currently the best available technologies, will significantly reduce system pressure by 10 to 20 PSIG (69 to 138 kPa) with a negligible impact on temperature.

The present system for purification of highly purified and ultra-pure water operates at 0.1 GPM (379 ml/min). The device has inlet tubing with an internal diameter (ID) of 0.375 inch (9.5 mm). Operating at 0.1 GPM (379 ml/min), the water flow is laminar with a Reynold's Number of approximately 900. The hydraulic design dimensions of the device components can change depending upon the downstream process requirements, enlarging or making smaller the piping or tubing and reaction chamber as needed. Alternatively, piping and tubing can be enlarged with multiple reaction chambers operating in parallel; these can be designed to meet any downstream hydraulic requirements. The hydraulic requirement will determine tubing/piping and component sizing that will maintain laminar flow (Reynold's Number less than 1,000) during the capture of contamination.

Referring again to FIG. 8, 0.1 GPM (379 ml/min) of highly purified or ultra-pure water enters the hydraulic component box 101 that works in conjunction with the electrical power and control box 55. Inside the hydraulic component box, the 0.375-inch (9.5 mm) ID tubing is connected to a capture variable area flowmeter (rotameter) 105. The capture flowmeter 105 and an integrated throttling valve monitor and control the flow during the capture cycle. The illustrative embodiment is designed for 0.1 GPM (379 ml/min) flow, but can operate successfully over a range of 0.026 to 0.16 GPM (100 to 600 ml/min). The incoming water is also connected to a flush variable area flowmeter (rotameter) 107 with an integrated throttling valve used during the release cycle as described below. The capture flowmeter 105 is connected to the reaction chamber 1 by 0.375-inch (9.5 mm) ID tubing. As the water moves through the reaction chamber, soluble and insoluble contamination is removed. The water purification process as described above, will capture contamination found within highly purified or ultra-pure water. Voltage during purification is typically between 75 and 125 VDC, although voltages outside this range have been used with similar results. Following the capture of contamination, clarified water exits the reaction chamber through a receiving conduit 110 in the form of 0.375-inch (9.5 mm) ID tubing to a solenoid-operated 3-way valve 111. During the capture cycle, water passes directly through the valve and exits the hydraulic component box as purified water 113.

For the configuration described above, the capture cycle typically lasts between 24 and 72 hours, depending upon the amount of contamination in the highly purified liquid (illustratively ultra-pure water). Longer capture cycles are possible by providing additional electrode surface area. Following the capture or purification cycle, the electrical power and control box 55 will automatically or manually:

1) Operate the three-way valve 111, redirecting system flow to waste 115.
2) Open the Flush flowmeter solenoid valve 109, increasing the flow in the 0.375-inch (9.5 mm) ID tubing and reaction chamber by 1.5 GPM (5,800 ml/min). The total system flow will increase to 1.6 GPM (6,179 ml/min), documented by the capture and flush flowmeters. Flow through the tubing and reaction chamber will become turbulent, with a Reynold's Number of approximately 14,000. The increased and turbulent flow also produces a linear liquid velocity inside the chamber that reduces contamination from being able to reach the opposite electrode during polarity reversal.
3) Increase voltage and reverse the polarity of the rod and tube electrodes.

The release voltage is determined by the individual water conditions (conductivity of water, charge characteristics of the retained particles, and concentration of contamination). However, it is typically 150% of the purification voltage. The polarity of the electrodes is alternated to ensure complete removal of the accumulated contamination, and followed by a non-powered flush where the electrodes are actively forced to zero volts (electrically short circuited to each other) to avoid inadvertent build up of static charges within the reaction cell. Static charge between electrodes could cause the retention of constituents during the flush operation.

An illustrative example of cycle timing and polarity of the water purification system is set out in Table 1.

TABLE 1

| Activity | Period of Time | Rod Polarity | Tube Polarity | Voltage |
|---|---|---|---|---|
| Capture Cycle[1] Release Cycle[2] | 48 hr | Positive | Negative | 100 VDC |
| 1$^{st}$ Polarity Reversal | 1 min | Negative | Positive | 150 VDC |
| 2$^{nd}$ Polarity Reversal | 1 min | Positive | Negative | 150 VDC |
| 3$^{rd}$ Polarity Reversal | 1 min | Negative | Positive | 150 VDC |
| 4$^{th}$ Polarity Reversal | 1 min | Positive | Negative | 150 VDC |
| 5$^{th}$ polarity Reversal | 1 min | Negative | Positive | 150 VDC |
| 6$^{th}$ Polarity Reversal | 1 min | Positive | Negative | 150 VDC |
| 7$^{th}$ Polarity Reversal | 30 sec | Negative | Positive | 150 VDC |
| 8$^{th}$ Polarity Reversal | 30 sec | Positive | Negative | 150 VDC |
| 9$^{th}$ Polarity Reversal | 30 sec | Negative | Positive | 150 VDC |
| 10$^{th}$ Polarity Reversal | 30 sec | Positive | Negative | 150 VDC |
| 11$^{th}$ Polarity Reversal | 30 sec | Negative | Positive | 150 VDC |
| 12$^{th}$ Polarity Reversal | 30 sec | Positive | Negative | 150 VDC |
| Flush Cycle[3] | 5 min | None | none | 0 Volts |

[1] 0.1 GPM (379 ml/min)
[2] 1.6 GPM (6179 ml/min)
[3] 1.6 GPM (6179 ml/min)
Total Release/Flush Time 14 min Following the release cycle, the device can be returned to the capture cycle. If the water purification device is idle for more than an hour, a release cycle would typically be run immediately prior to a capture cycle.

The performance of the water purification system, as described above, has been documented and is effective at improving the quality highly purified or ultra-pure water by removing constituent contamination.

Using an optical particle counter (OPC) manufactured by Particle Measuring Systems, Inc. (Model M50), the water purification system removed approximately 80% of all particles greater than 50 nm. Utilizing SEM analytical technique, the water purification system removed approximately 71% of all particles greater than 200 nm. Importantly, both analytical methods documented large concentration of particles being released during release cycle (polarity reversal), confirming that the water purification device retains particles during the capture cycle.

Significantly, both the OPC and SEM techniques documented an increase in the particle size distribution during particle release cycle, indicating that particle agglomeration was occurring during the capture cycle.

Furthermore the SEM technique was able to compare the mass of particles or contamination between the capture and release cycles. This evaluation indicated that the release cycle particles had approximately 300% more mass. This increase in mass validates that the water purification system is removing and agglomerating particles, nanoparticles, colloids, molecules, and ions small than the SEM analytical detection limit. Simply stated, particles smaller than 200 nm within the ultra-pure supply water were captured and agglomerated and later released as particles greater than 200 nm during the release cycle.

OPC and SEM analytical testing has validated that the water purification system effectively improves highly purified and ultra-pure water. Importantly, the OPC data confirms that sub-50 nm particles are being captured and agglomerated.

C. Analytical System—Design and Operation

Figure 9:
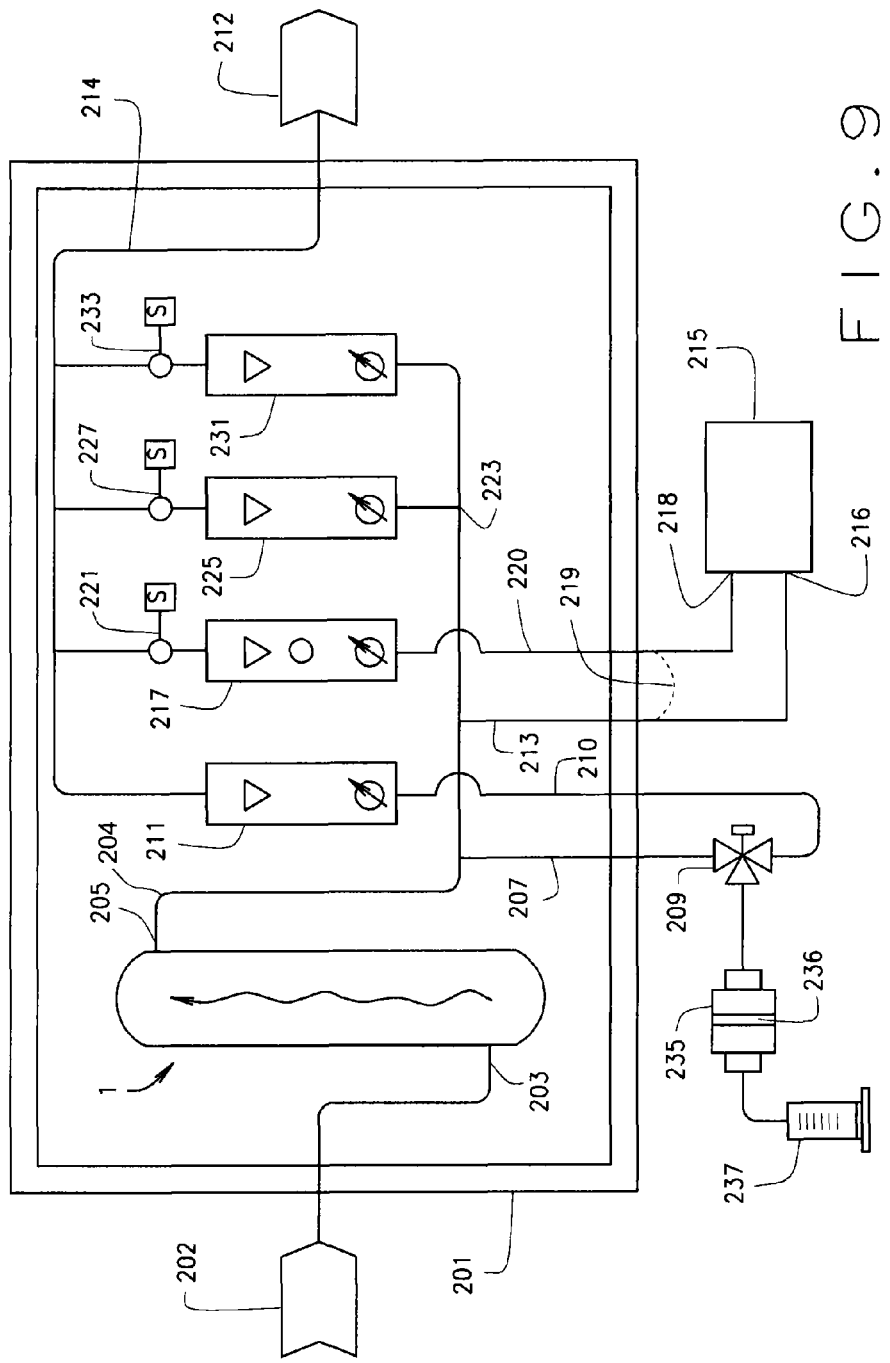
FIG. 9 is a schematic diagram illustrating the apparatus and the hydraulic components used in a system for the analytical evaluation of highly purified and ultra-pure water.

FIG. 9 is a schematic of the hydraulic components located within a hydraulic component box 201, and works in conjunction with an electrical power and control box. The piping and component layout is a close representation of the system design, with the box orientated in the vertical position (top of the figure is up). All wetted surfaces associated with the tubing, fittings and system components are made from polyvinylidene fluoride (PVDF), Hylar, or Teflon high purity materials so as not to not add any contamination to the incoming water. Except for the reaction chamber, all components are available as standard parts from high purity water piping suppliers.

Referring now to FIG. 9, highly purified or ultra-pure water described above enters the hydraulic component box 201 from water supply 202. The inlet water pressure and temperature will be determined by the sampling location, but it is anticipated to vary between 20 and 80 pounds per square inch gauge (PSIG) (138 to 552 kPa) and between 1 and 90 degrees C. The illustrative embodiment of the system operates at 0.1 GPM (379 ml/minute) during particle capture. The device has inlet tubing with an internal diameter (ID) of 0.375 inch. Operating at 0.1 GPM (379 ml/min), the water flow is laminar with a Reynold's Number of approximately 900. Properly designed, a larger sampling flowrate will collect additional contamination during an equivalent period of time. The specific sampling flowrate will determine tubing/piping and component sizing. However, it is important to maintain laminar flow (Reynold's Number less than 1,000) during the capture of contamination.

Highly purified or ultra-pure water 202 enters the hydraulic component box 201 and is connected to the inlet 203 of the reaction chamber 1. As the water moves upward through the chamber, soluble and insoluble contamination is removed. Following the removal of contamination, clarified water exits the outlet 205 of the reaction chamber 1 and enters a receiving conduit 204. At SEM sample line 207, a 100 ml/minute flow is split from the primary flow stream (379 ml/min). The 0.125-inch (3.2 mm) (ID) SEM sample line 207 exits the bottom of the hydraulic component box 201 and is connected to a three-way valve 209. During the capture of contamination, the valve 209 bypasses the sample membrane and directs flow back to the hydraulic component box. This allows a SEM holder 235 to be installed or removed without spillage of the liquid to be analyzed. Inside the box, the 0.125-inch (3.2 mm) (ID) tubing 210 from the valve 209 is connected to the SEM variable area flowmeter (rotameter) 211. To ensure proper flow rate, the SEM flowmeter 211, with a built-in throttling valve, is set at 100 ml/min. The SEM flowmeter 0.125-inch (3.2 mm) (ID) exit tubing is connected to a larger 0.375-inch (9.5 mm) (ID) outlet header 214, discharging the water 212 outside of the hydraulic component box (waste or recycle).

Referring again to FIG. 9, at particle counter sample line 213, an additional 100 ml/minute of flow is split from the primary flow stream (279 ml/min remaining). The 0.125-inch (3.2 mm) (ID) sample line exits the bottom of the hydraulic component box and is connected to an optical particle counter (OPC) 215 at its inlet 216. It may be noted that optical particle counters typically require 100 ml/min sample flow. The flow from the OPC outlet 218 is returned to the hydraulic component box in a 0.125-inch (3.2 mm) (ID) tube 220 and is routed to the OPC variable area flowmeter (rotameter) 217 that controls and monitors the flowrate. The OPC 215 is used for monitoring the water quality during the capture of contamination and more importantly monitors water quality during the release of contamination discussed below. The OPC 215 is not required to operate the system. If an OPC is not used, a loop connection 219 is installed to maintain the specified flow rate of 100 ml/min and prevent a dead leg that would result from capping the ports. The OPC flowmeter 0.125-inch (3.2 mm) (ID) exit tubing is connected to an on/off solenoid valve 221 controlled from the electrical power and control box. During the capture of contamination, the valve is in the open position. Following the OPC flowmeter solenoid valve 221, a 0.125-inch (3.2 mm) tube connects to the larger 0.375-inch (9.5 mm) (ID) outlet header 214, discharging the water 212 outside of the hydraulic component box (waste or recycle).

Still referring to FIG. 9, at point 223, the remaining flow of 179 ml/min water within a 0.375-inch (9.5 mm) tube is directed to the primary flow (PF) variable area flowmeter (rotameter) 225, where it is controlled and monitored. The PF flowmeter's 0.125-inch (3.2 mm) (ID) exit tubing is connected to an on/off solenoid valve 227 controlled from the electric power and control box. During the capture of contamination, the valve 227 is in the open position. The PF flowmeter's 0.375-inch (9.5 mm) (ID) exit tubing is connected to the 0.375-inch (9.5 mm) (ID) outlet header 214 and the water is then discharged, with the SEM and OPC streams from the hydraulic component box at 212.

At point 223, the 0.375-inch (9.5 mm) tubing also terminates at a flush variable area flowmeter (rotameter) 231. The flush solenoid valve 233 located at the exit of the flush flowmeter, is closed during the capture cycle.

The capture cycle as described above, will retain contamination found within highly purified or ultra-pure water. The capture cycle time will vary depending upon the contamination level in the sample water. For the above configuration, useful capture times varied between 6 and 48 hours. The longer sample time will collect more contamination for analysis. However, if the electrodes become saturated, additional capture time is ineffective. The capture voltage is between 50 and 150 volts DC in this example and is typically between 75 and 125 volts DC.

The capture of contamination is followed by the release of accumulated constituents from the reaction chamber electrodes. After the programmed capture period, the controller (automatically or manually) will reverse the DC polarity, releasing the concentrated and agglomerated contamination. The polarity is cycled to ensure the complete release of contamination. The typical voltage during polarity reversal is 150% of the capture voltage. Immediately prior to the first polarity reversal, the primary flow solenoid valve 227 is closed, forcing all of the concentrated contamination through the SEM and OPC sample lines. It will be seen that the flush solenoid valve 233 will remain closed. The concentrated contamination can be documented by the OPC. If the OPC is not installed (operating with by-pass loop 219), then the system can be programmed to close the OPC solenoid valve 221, forcing all of the concentrated contamination to the SEM sample line. In order to collect the released contamination for analysis, the 3-way valve 209 is operated prior to polarity reversal, directing the SEM sample flow to a 25 mm filter holder 235 containing a 200, 100, or 50 nm pore SEM sampling membrane 236. The flowrate through a SEM sample membrane varies initially between 50 and 100 ml/min depending upon the pressure and temperature of the water and membrane pore size. As the membrane loads up with contamination, the flow rate may decrease even further. A graduated cylinder 237 located on the outlet of the SEM membrane holder will measure total volume of water collected during the typical nine-minute release cycle, permitting calculation of contaminant concentrations. At the end of the nine-minute release cycle, the 3-way valve 209 is returned to the original position, which will re-direct water to the SEM flowmeter 211.

After the release of contamination to the sampling membrane, the system receives a powered flush by opening the flush solenoid valve 233 and allowing the system flow to increase by 1.5 GPM (5,800 ml/min). The total system flow during the powered flush cycle will be 1.6 GPM (6,179 ml/min) as documented by the SEM, OPC, primary flow, and flush flowmeters 211, 217, 225, and 231. The flow during the flush cycle will be turbulent, having a Reynold's Number of approximately 14,000. In addition to turbulent flow, the polarity of the electrodes is cycled every 30 seconds at typically 150% of capture voltage for a total of four minutes to ensure the release of any remain contamination. The powered flush is followed by a five minute non-powered flush. During the non-powered flush, the electrodes must be actively forced to zero volts to avoid the build-up of static charges within the reaction chamber. Static charge between electrodes could cause the undesired retention of constituents during the flush cycles. The SEM membrane holder 235, including the membrane 236, is transferred to a laboratory for analysis. The laboratory's analysis of the membrane will determine particle sizing, concentration, and elemental analysis by SEM/EDS.

An illustrative example of cycle timing and polarity of the analytical system is set out in Table 2.

TABLE 2

| Activity | Period of Time | Rod Polarity | Tube Polarity | Voltage |
|---|---|---|---|---|
| Capture Cycle[1] | 24 hr | Positive | Negative | 100 VDC |
| Release Cycle[2] | | | | |
| 1st Polarity Reversal | 1 min | Negative | Positive | 150 VDC |
| 2nd Polarity Reversal | 1 min | Positive | Negative | 150 VDC |
| 3rd Polarity Reversal | 1 min | Negative | Positive | 150 VDC |
| 4th Polarity Reversal | 1 min | Positive | Negative | 150 VDC |
| 5th polarity Reversal | 1 min | Negative | Positive | 150 VDC |
| 6th Polarity Reversal | 1 min | Positive | Negative | 150 VDC |
| 7th Polarity Reversal | 30 sec | Negative | Positive | 150 VDC |
| 8th Polarity Reversal | 30 sec | Positive | Negative | 150 VDC |
| 9th Polarity Reversal | 30 sec | Negative | Positive | 150 VDC |
| 10th Polarity Reversal | 30 sec | Positive | Negative | 150 VDC |
| 11th Polarity Reversal | 30 sec | Negative | Positive | 150 VDC |
| 12th Polarity Reversal | 30 sec | Positive | Negative | 150 VDC |
| Total Release Time 9 min (End of the SEM sampling) | | | | |
| Power Flush Cycle[3] | 30 sec | Negative | Positive | 150 VDC |
| | 30 sec | Positive | Negative | 150 VDC |
| | 30 sec | Negative | Positive | 150 VDC |
| | 30 sec | Positive | Negative | 150 VDC |
| | 30 sec | Negative | Positive | 150 VDC |
| | 30 sec | Positive | Negative | 150 VDC |
| | 30 sec | Negative | Positive | 150 VDC |
| | 30 sec | Positive | Negative | 150 VDC |
| Unpowered Flush Cycle Total Flush Time 9 min | 5 min | none | none | 0 VDC |

[1] 0.1 GPM (379 ml/min)
[2] 0.013-0.053 GPM (50-200 ml/min) depending on flow rate through membrane and whether OPC connected to system
[3] 1.6 GPM (6179 ml/min)

The analytical apparatus can be installed and used to track baseline water or moved to various locations to determine site-specific water quality conditions.

Following the release cycle described above, the SEM filter holder and membrane would be sent to a laboratory skilled in the evaluation of SEM ultra-pure water sample membranes. The SEM is able to resolve and photograph individual particles greater than 50 nm and elementally evaluate particles larger than 100 nm using EDS. Knowing the original sample volume from the graduated cylinder 237, will allow the analyst to determine the concentration and particle size distribution of particles within the water sample filtered through the SEM membrane, thus providing important information regarding the concentration of contamination within highly purified and ultra-pure water.

The analytical system has been tested. The SEM/EDS technique has identified more than 20 elements. The most common elemental constituents include carbon particle (likely biological material); silica/oxygen/particle; iron/chrome/nickel/oxygen particle; and fluorine/carbon/oxygen particle The ability to determine particle morphology, concentration, and element composition is important to the proper operation of a highly purified and ultra-pure water system.

Numerous variations in the device, methods, and systems of the present invention will occur to those skilled in the art, and parts of the present invention will immediately be recognized to have applications in other areas. The scope of the invention is thus determined by the appended claims, rather than by the specific examples of the best mode of practicing the invention disclosed hereinabove.

The invention claimed is:

1. A method of extracting trace amounts of contaminants from high resistivity liquid having a bulk resistivity of greater than 1.0 megohm-centimeter, said method comprising the steps of:
   flowing in laminar fashion the liquid to be purified through an elongate cylindrical chamber, a wall of the chamber forming an outer electrode, the chamber having a central axial electrode therein;
   providing an electromagnetic field in the chamber transverse to the direction of flow to cause the contaminants to deposit and agglomerate on the electrodes in a removal zone of the chamber;
   drawing substantially all the liquid from the chamber to a receiving conduit; and periodically reversing the electromagnetic field to remove contaminants and agglomerated contaminants from the removal zone of the electrodes.

2. The method of claim 1 wherein reversing the electromagnetic field is at a magnitude greater than the capture magnitude.

3. The method of claim 1 wherein the contaminants comprise inorganic particles and organic particles.

4. The method of claim 1 wherein dissolved contaminants are deposited and agglomerated on the electrodes.

5. The method of claim 1 comprising a further step of pre-charging contaminants using chemical, ultraviolet, or electromagnetic energy to partially oxidize or charge-modify insoluble and soluble contaminants before they enter the elongate cylindrical chamber.

6. The method of claim 1 wherein the contaminants are not pre-charged before they enter the elongate cylindrical chamber.

7. The method of claim 1 wherein the liquid flows into the elongate cylindrical chamber in turbulent fashion, and flow becomes laminar within the chamber.

8. The method of claim 1 wherein the step of periodically reversing the electromagnetic field comprises flowing the liquid in the removal zone of the elongate cylindrical chamber in turbulent fashion.

9. The method of claim 1 further comprising electrically short circuiting the electrodes to each other while the electromagnetic field is not present.

10. The method of claim 1 further comprising determining contamination levels in the liquid by measuring current between the electrodes.

11. The method of claim 1 further comprising controlling at least one of the steps of the method in accordance with measured levels of contamination in the highly purified liquid.

12. The method of claim 1 further including a step of passing particles removed from the electrodes to a filter for collection and analysis.

13. The method of claim 1 wherein the liquid is highly purified water and wherein further-purified water from the receiving conduit is used in an industrial process.

14. The method of claim 1 comprising establishing a field strength in excess of 5300 volts per meter between the axial electrode and the chamber wall.

15. The method of claim 1 wherein the length of the chamber is at least twenty times its inner diameter.

16. The method of claim 1 wherein the distance between the axial electrode and the chamber wall is less than one-half inch.

17. The method of claim 1 wherein the chamber lacks square corners and dead zones.

18. The method of claim 1 further comprising insulating a portion of the axial electrode at each end of the electrode, but not insulating a central portion of the axial electrode.

19. The method of claim 1 further comprising sealing the chamber to a first block by an O-ring seated in a groove in an outlet end of the chamber, a radially inward part of the groove communicating with the interior of the cylinder, a radially outward part of the groove being axially deeper than the radially inward part.

20. The method of claim 1 wherein the step of periodically reversing the electromagnetic field is controlled by a timer.

21. The method of claim 1 wherein the step of periodically reversing the electromagnetic field is controlled by sensing a parameter related to the level of contamination in the high-resistivity liquid.

22. The method of claim 1 wherein at least one of the rate of laminar flow and the electromagnetic field strength during laminar flow is controlled by sensing a parameter related to the level of contamination in the high-resistivity liquid.

23. The method of claim 1 wherein substantially all the liquid drawn into the receiving conduit is delivered to an industrial process.

24. The method of claim 1 wherein the liquid is water.

25. The method of claim 24 wherein the water has a bulk resistivity between about 1 megohm-cm and about 18 megohm-cm.

26. The method of claim 1 comprising agglomerating at least some particles smaller than 50 nm to particles larger than 50 nm.

27. The method of claim 26 wherein more of the released particles have a diameter larger than 50 nm than in the high resistivity liquid entering the chamber.

28. The method of claim 1 wherein the step of periodically reversing the electromagnetic field comprises a series of polarity reversals.

29. The method of claim 28 wherein the step of periodically reversing the electromagnetic field is controlled by time or by a sensed condition.

30. The method of claim 1 wherein the electromagnetic field is an electric field established by a voltage of less than six hundred volts.

31. The method of claim 30 wherein the electric field is established by a DC voltage of seventy-five to one hundred-fifty volts.

32. The method of claim 1 further comprising attaching at least one valve to an outlet of the chamber and attaching a control to the valve and to a source of DC voltage.

33. The method of claim 32 wherein, the control causes the valve to direct flow to a filter and produces a series of reverse-polarity pulses to release agglomerated particles from the electrodes and carry them to the filter.

34. The method of claim 1 wherein removed contaminants and agglomerated contaminants are captured and analyzed.

35. The method of claim 34 further comprising initiating a capture cycle on receipt of an external signal that an upset has occurred in a liquid being analyzed.

36. The method of claim 35 further comprising analyzing at least one of the size, composition, and concentration of particles captured.

37. The method of claim 1 wherein the central electrode has an uninsulated central removal zone and an insulative coating on at least an outlet end of the electrode.

38. The method of claim 37 wherein the central electrode has an insulative coating at each of its ends.

39. The method of claim 37 wherein the central electrode comprises a rod.

* * * * *